United States Patent [19]

Guillen

[11] Patent Number: Plant 7,670

[45] Date of Patent: Oct. 8, 1991

[54] NEW GUINEA IMPATIENS PLANT NAMED CELEBRATION CANDY PINK

[75] Inventor: Mario A. Guillen, Cargato, Costa Rica

[73] Assignee: Ball Seed Co., West Chicago, Ill.

[21] Appl. No.: 531,548

[22] Filed: Jun. 1, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A distinct New Guinea Impatiens plant named Celebration Candy Pink characterized by its iridescent, medium pink flower color with darker pink radiating lines and eye, large flowers, spreading and compact growth habit, dark green leaves and floriferous habit.

1 Drawing Sheet

The present invention relates to a new and distinctive cultivar of New Guinea Impatiens plant, botanically known as New Guinea Impatiens and known by the cultivar name Celebration Candy Pink. The new cultivar was developed by me through controlled breeding by crossing the cultivar identified as Linda Vista selection #417 with the cultivar identified as Linda Vista selection #598. Both cultivars are selections of Pan American Seed, Linda Vista, Costa Rica.

Asexual reproduction by terminal cuttings taken at West Chicago, Ill., has shown that the unique features of this New Guinea Impatiens are stabilized and are reproduced true to type in successive propagations.

The following characteristics in combination distinguish the new Impatiens from other cultivar impatiens of this type known and used in the floriculture industry.

1. Medium pink flower color with darker pink radiating lines and dark eye; iridescent.
2. Spreading and compact habit.
3. Floriferous habit.
4. Large flowers.
5. Non-variegated foliage.
6. Flowers are positioned above the foliage in uniform display.

The new cultivar is somewhat similar in flower color (although a deeper pink) to the cultivar Enterprise disclosed in U.S. Plant Pat. No. 5,868, with which Celebration Candy Pink can be compared. Reference is made to attached Chart A which compares characteristics of the respective cultivars. To summarize, compared to Enterprise, Celebration Candy Pink has a more uniform and compact habit, flowers which are held above the foliage in a uniform display, more freely flowering, non-variegated foliage, and larger flowers which are a deeper pink in color.

The accompanying colored photograph illustrates the overall appearance of this cultivar, showing colors as true as it is reasonably possible to obtain in a colored reproduction of this type.

The following is a detailed description of my new New Guinea Impatiens cultivar based on plants produced under commercial practice in West Chicago, Ill., in a glass-covered greenhouse with day temperatures of 24° to 26° C. and night temperatures of 18° to 20° C.

Color references are made to The Royal Horticultural Society Colour Chart except where general terms of ordinary dictionary significance are used.

Propagation:

A. *Type cutting.*—Terminal tip.

B. *Time to initiate roots.*—5 days at 24° C. summer; 7 days at 21° C. winter.

C. *Rooting habit.*—Fibrous, branching.

Plant description:

A. *Form.*—Freely branching, vigorous.

B. *Habit of growth.*—Spreading and upright but compact habit, 22 cm. by 24 cm. asymmetrical.

C. *Foliage.*—1. Size: 10 to 12 cm. in length, 3.5 to 4.0 cm. wide. 2. Shape: Lanceolate, acuminate tip with attenuate base. 3. Texture: Smooth. 4. Margin: Finely serrated. 5. Color: Dark green with red venation. Young foliage: Top side 147A; under side 59A. Mature foliage: Top side 147A; under side 59A. 6. Variegation: None. 7. Venation: 59A.

Flowering description:

A. *Flowering habits.*—Freely flowering.

B. *Natural flowering season.*—Year-round in greenhouse environment.

C. *Flower bud shape and color.*—Conical, 59B.

D. *Flower borne.*—Above foliage, arising from leaf axils.

E. *Quantity of flowers.*—10 to 12 per branch.

F. *Petals.*—1. Shape: Cordate. 2. Color: Pink bicolor with dark eye (66C), iridescent. Top side when opening 65B with radiating lines of 66B which mature to 66C; fading to 65D with 66C radiating lines. Under side 65B with radiating lines 66C. 3. Number of petals: 5. 4. Size of flowers: 6 cm (width)×6 cm (length).

G. *Reproductive organs.*—1. Stamens: 5 in number. a. Anther shape: Oblong. b. Anther color: 11D. c. Pollen color: 10D. 2. Pistils: a. Stigma shape: Round. b. Stigma color: 59A. c. Style color: 59A. d. Ovary number: Superior, 5-celled. e. Ovary size: 1.5 cm (length). f. Ovary color: 59B.

Disease resistance: No fungal or bacterial problems observed.

CHART A

| Characteristic | Celebration Candy Pink | Enterprise |
|---|---|---|
| Plant height | 9 cm | 14 cm |
| Plant diameter | 22 cm. by 24 cm.; asymmetrical | 22–26 cm |

-continued

CHART A

| Characteristic | Celebration Candy Pink | Enterprise |
|---|---|---|
| Branches/plant | 5 | 6 |
| Foliage color | 147A, no | 147A, variegated |
| Top side | variegation | with 154B |
| Flower color | 65B with 66C | 66D with faint |

-continued

CHART A

| Characteristic | Celebration Candy Pink | Enterprise |
|---|---|---|
| Top side | radiating lines and eye | radiating lines |
| Flower size | 6 cm × 6 cm | 5 cm × 4 cm |

I claim:

1. A new and distinct cultivar of New Guinea Impatiens plant named Celebration Candy Pink, as illustrated and described.

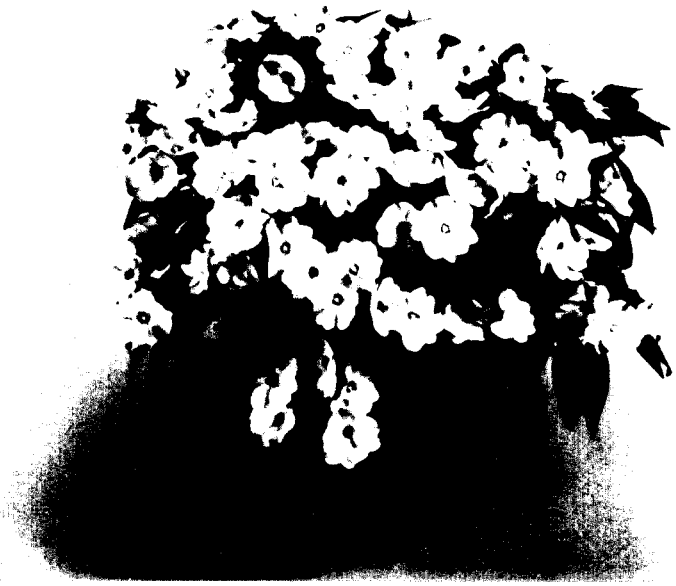

* * * * *